(12) United States Patent
Aranda Hernandez

(10) Patent No.: US 12,201,433 B2
(45) Date of Patent: Jan. 21, 2025

(54) DETECTION AND LOCALIZATION OF MYOCARDIAL INFARCTION USING VECTORCARDIOGRAPHY

(71) Applicant: Medtronic, Inc., Minneapolis, MN (US)

(72) Inventor: Alfonso Aranda Hernandez, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 490 days.

(21) Appl. No.: 17/452,367

(22) Filed: Oct. 26, 2021

(65) Prior Publication Data
US 2022/0125365 A1    Apr. 28, 2022

Related U.S. Application Data

(60) Provisional application No. 63/106,639, filed on Oct. 28, 2020.

(51) Int. Cl.
*A61B 5/341* (2021.01)
*A61B 5/355* (2021.01)
*A61B 5/366* (2021.01)
*G16H 50/20* (2018.01)
*G16H 50/70* (2018.01)

(52) U.S. Cl.
CPC .............. *A61B 5/341* (2021.01); *A61B 5/355* (2021.01); *A61B 5/366* (2021.01); *G16H 50/20* (2018.01); *G16H 50/70* (2018.01)

(58) Field of Classification Search
CPC ......... A61B 5/341; A61B 5/355; A61B 5/366; G16H 50/70; G16H 50/20
See application file for complete search history.

(56) References Cited

U.S. PATENT DOCUMENTS

| | | | |
|---|---|---|---|
| 7,266,408 B2* | 9/2007 | Bojovic | A61B 5/341 600/512 |
| 10,039,468 B2* | 8/2018 | Gupta | A61B 5/349 |
| 11,311,230 B2* | 4/2022 | Sullivan | A61B 5/021 |
| 2016/0135706 A1* | 5/2016 | Sullivan | A61B 5/0533 600/509 |
| 2017/0340887 A1* | 11/2017 | Engels | A61N 1/36592 |
| 2019/0216350 A1 | 7/2019 | Sullivan et al. | |
| 2022/0125365 A1* | 4/2022 | Aranda Hernandez | G06N 5/01 |

OTHER PUBLICATIONS

Acharya et al., "Automated detection and localization of myocardial infarction using electrocardiogram: a comparative study of different leads", Knowledge-Based Systems. vol. 99, Jan. 2016, pp. 146-156.

(Continued)

*Primary Examiner* — Shirley X Jian
(74) *Attorney, Agent, or Firm* — Shumaker & Sieffert, P.A.

(57) ABSTRACT

A method includes detecting whether one or more myocardial infarctions (MI) has occurred using vectorcardiographic (VCG) signals with gradient boosting, the VCG signals including VCG loops, and determining an MI location using the VCG signals and gradient boosting.

16 Claims, 16 Drawing Sheets

(56) References Cited

OTHER PUBLICATIONS

Aranda et al., "Performance of Dower's Inverse Transform and Frank Lead System for Identification of Myocardial Infarction", 37th Annual International Conference of the IEEE Engineering in Medicine and Biology Society (EMBC), Nov. 5, 2015, pp. 4495-4498.

Bousseljot, "PTB Diagnostic ECG Database", Sep. 25, 2004, 3 pp. Retrieved from the Internet: https://www.physionet.org/content/ptbdb/1.0.0/.

Chapelle et al. "Yahoo! Learning to Rank Challenge Overview", JMLR: Workshop and Conference Proceedings 14, Jun. 2011, 24 pp.

Correa et al., "Novel set of vectorcardiographic parameters for the identification of ischemic patients", Medical Engineering & Physics, Mar. 12, 2012, 13 pp.

Frank, "A Direct Experimental Study of Three Systems of Spatial Vectorcardiography", American Heart Association Circulation, vol. X, Jul. 1954, pp. 101-113.

Frank, "An Accurate, Clinically Practical System for Spatial Vectorcardiography", American Heart Association Circulation, vol. XIII, May 1956, pp. 737-749.

Friedman et al. "Additive Logistic Regression: A Statistical View of Boosting", The Annals of Statistics, vol. 28, No. 2, Apr. 2000, pp. 337-407.

Friedman, "Stochastic gradient boosting", Computational Statistics & Data Analysis 38, 2002 (Applicant points out, in accordance with MPEP 609.04(a), that the year of publication, 2002, is sufficiently earlier than the effective U.S. filing date, so that the particular month of publication is not in issue.) pp. 367-378.

Goldberger et al. "PhysioBank, PhysioToolkit, and PhysioNet: components of a new research resource for complex physiologic signals", American Heart Association Circulation, vol. 101, No. 23, Jun. 13, 2000, 6 pp.

Han et al., "Automated interpretable detection of myocardial infarction fusing energy entropy and morphological features", Computer Methods and Programs in Biomedicine, vol. 175, Jul. 2019, pp. 9-23.

Hernandez et al., "Myocardial Ischemia Diagnosis Using a Reduced Lead System", 2018 40th Annual International Conference of the IEEE Engineering in Medicine and Biology Society (EMBC), Jul. 2018, 4 pp.

Hernandez, "Automated detection and localization of myocardial infarction using vectorcardiography", Journal of Knowledge-Based Systems, Jul. 24, 2020, 29 pp.

International Search Report and Written Opinion of International Application No. PCT/US2021/072087, dated Feb. 9, 2022, 11 pp.

Liu et al., "MFB-CBRNN: A Hybrid Network for MI Detection Using 12-Lead ECGs", IEEE Journal of Biomedical and Health Informatics, vol. 24, Issue 2, Feb. 2020, pp. 503-514.

Mathers et al., "WHO methods and data sources for country-level causes of death 2000-2016", Department of Information, Evidence and Research WHO, Mar. 2018, 65 pp.

Reasat et al. "Detection of Inferior Myocardial Infarction using Shallow Convolutional Neural Networks", 2017 IEEE Region 10 Humanitarian Technology Conference (R10-HTC), Dec. 21-23, 2017, pp. 718-721.

Ridgeway, "Generalized Boosted Models: A guide to the gbm package", Aug. 3, 2007, 12 pp.

Thygesen et al., "Third universal definition of myocardial infarction", European Heart Journal—Expert Consensus Document, Aug. 24, 2012, 18 pp.

Virani et al., "Heart Disease and Stroke Statistics—2020 Update", American Heart Association Circulation, Mar. 3, 2020, 458 pp.

Yang et al., "Identification of myocardial infarction (MI) using spatio-temporal heart dynamics", Medical Engineering & Physics, Aug. 17, 2011, 13 pp.

Zhang et al. "Atlas-Based Quantification of Cardiac Remodeling Due to Myocardial Infarction", PLOS ONE, vol. 9, Issue 10, Oct. 2014, 13 pp.

Zhang et al., "An up-to-date comparison of state-of-the-art classification algorithms", Expert Systems With Applications, vol. 82, Apr. 2017, pp. 128-150.

* cited by examiner

DETECTION AND LOCALIZATION OF MYOCARDIAL INFARCTION USING VECTORCARDIOGRAPHY

This application claims the benefit of U.S. Provisional Application Ser. No. 63/106,639, filed Oct. 28, 2020, the entire content of which is incorporated herein by reference.

TECHNICAL FIELD

The disclosure relates to medical devices and methods thereof, and, more particularly, to methods that detect and identify a location of a myocardial infarction.

BACKGROUND

Coronary heart diseases are one of the leading causes of death worldwide. Myocardial Infarction (MI), also known as a heart attack, is an example of a coronary heart disease that occurs when blood flow decreases or stops to a part of the heart, resulting in an imbalance between oxygen supply and demand, causing damage to the heart muscle. Morbidity and mortality from MI can be significantly reduced when symptoms (chest pain, shortness of breath, etc.) are recognized early enough, reducing time to treatment. The expansion and effect on left ventricular (LV) contractility can be better contained when MI is identified early and quickly. As such, time to treatment for MI patients can be a matter of life and death.

SUMMARY

In general, identification and interpretation of changes occurring in an electrocardiogram (ECG) are an essential part of the diagnostic work-up of patients with suspected MI. Common ECG manifestations of MI are ST elevation (where ST refers to the region between the end of ventricular depolarization and beginning of ventricular repolarization on the ECG), ST depression and T-wave changes and abnormalities. Various ECG lead systems have been developed and improved, and a 12-lead ECG is a standard extensively used in diagnosing the cardiac disease. Nonetheless, despite the availability of such systems, it may not be possible in actual clinical practice to extract relevant information from ECG signals to derive MI locations using known techniques.

Accordingly, this disclosure describes techniques for detecting whether one or more MI have occurred, as well as MI locations, using vectorcardiography (VCG) signals with gradient boosting. VCG is able to capture spatial and temporal information of heart's electrical forces which can assist to localize the MI region. The orthogonal Frank's VCG lead system uses fewer leads compared to the 12-lead ECG system, and may capture more non-redundant information than the 12-lead ECG system. For example, VCG signals may contain spatial and temporal information on heart's electrical forces. In some instances, VCG signals may provide information on spatial propagation and orientation of heart's electrical forces via a three-dimensional vector, which might be particularly important for MI location assessment.

In an example, a method includes detecting whether one or more myocardial infarctions (MI) has occurred using VCG signals with gradient boosting, the VCG signals including VCG loops; and determining an MI location using the VCG signals with gradient boosting.

In an example, a system includes a set of electrodes configured to sense VCG signals; and processing circuitry configured to: detect whether one or more myocardial infarctions (MI) has occurred using the VCG signals with gradient boosting; and determine a MI location using the VCG signals and gradient boosting.

In an example, a non-transitory computer-readable storage medium includes instructions that, when executed, cause processing circuitry to: detect whether one or more myocardial infarctions (MI) has occurred using vectorcardiographic (VCG) signals with gradient boosting, the VCG signals including VCG loops; and determine an MI location using the VCG signals with gradient boosting if one or more myocardial infarctions are detected.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

Generally, this disclosure describes techniques for detecting whether and where one or more myocardial infarctions (MI) has occurred using vectorcardiopgraphy (VCG) signals with gradient boosting. The improvements, particularly in relation to therapy, include early MI location, which reduces time to treatment. For example, the method may be conducted in the ambulance on the way to a hospital and the information may be sent to the hospital before the patient arrives. In addition, the treatment may be less expensive because MRI may not be needed for MI location determination. The method may be well suited for emerging countries where MRI access is limited or unavailable.

Figure 14:
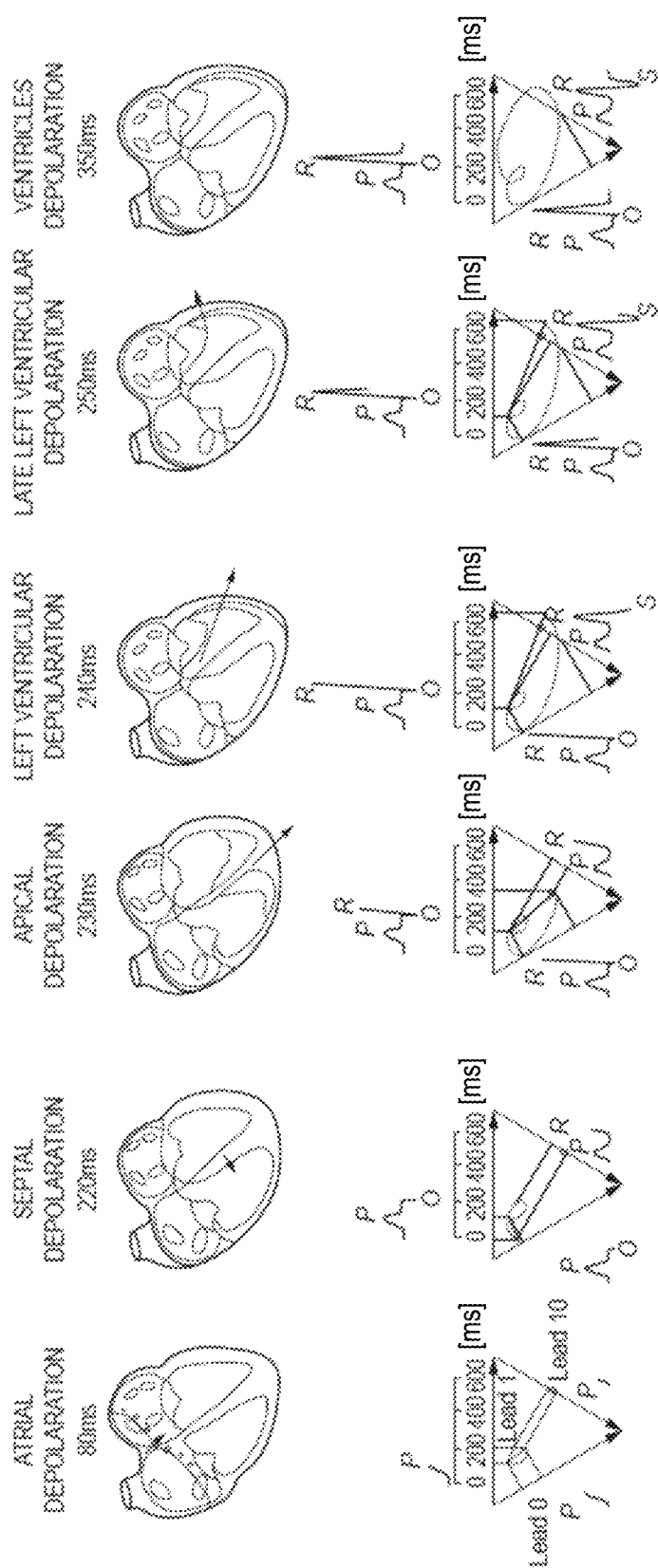
FIG. 14 illustrates VCG loops and ECG plotted together during a heart's depolarization phase.
Figure 15:
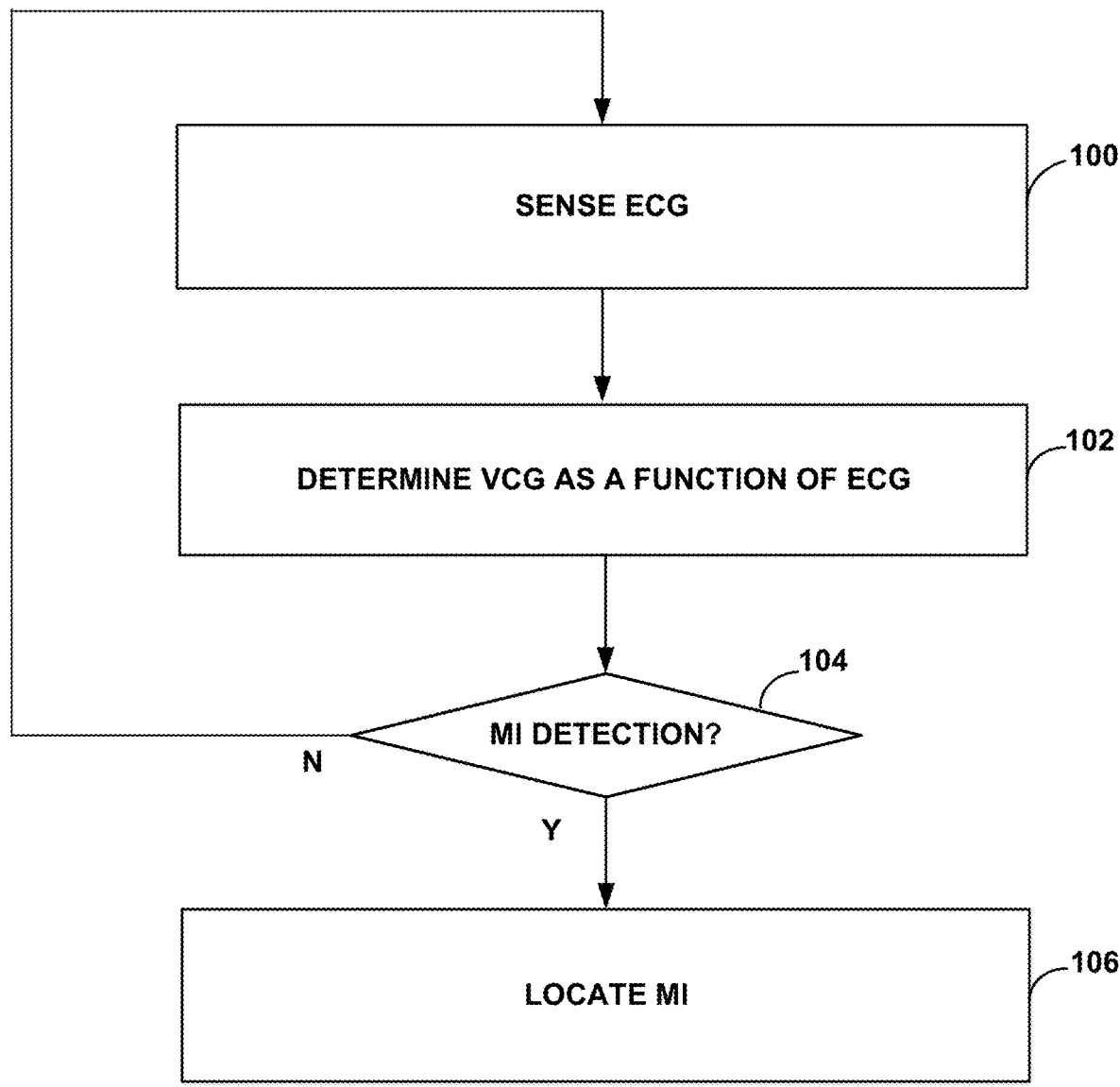
FIG. 15 illustrates a flow diagram of an example method for detecting and localizing MI in accordance with techniques of this disclosure.

In some examples, a method includes detecting whether one or more MIs have occurred using VCG signals with gradient boosting, the VCG signals including VCG loops, and determining an MI location using the VCG signals if a MI has been detected (See FIG. 15). VCG signals provide information about the spatial propagation and orientation of the heart's electrical forces as shown in FIG. 14, where VCG loops and ECG are plotted together during the heart's depolarization phase.

In some examples, Gradient Boosting Method (GBM) is used to build a model. A GBM model may have fewer hyperparameters that require tuning than a Convolutional Neural Network (CNN). GBM may be used to solve both regression and classification problems. GBM may represent an ensemble of single regression trees built in a greedy fashion, generating a predictive model in the form of an ensemble of weak prediction models. GBM trees may combine gradient boosting with bootstrap bagging. In this way, GBM may improve implementations of machine learning with respect to non-linear functions. For instance, in each iteration of a machine learning algorithm, a new decision tree model may be built based on the residuals of the previous decision trees.

In some examples, a method includes MI detection and MI location by using VCG derived parameters as well as GBM. The method is able to capture spatial and temporal information of heart's electrical forces, which may assist properly locating the MI region. For this reason, this method may be superior to the standard 12-lead ECG for assessing MI location. Furthermore, using a reduced lead system may simplify preparation and execution of medical procedures and enable the possibility of remote monitoring.

Figure 1A:
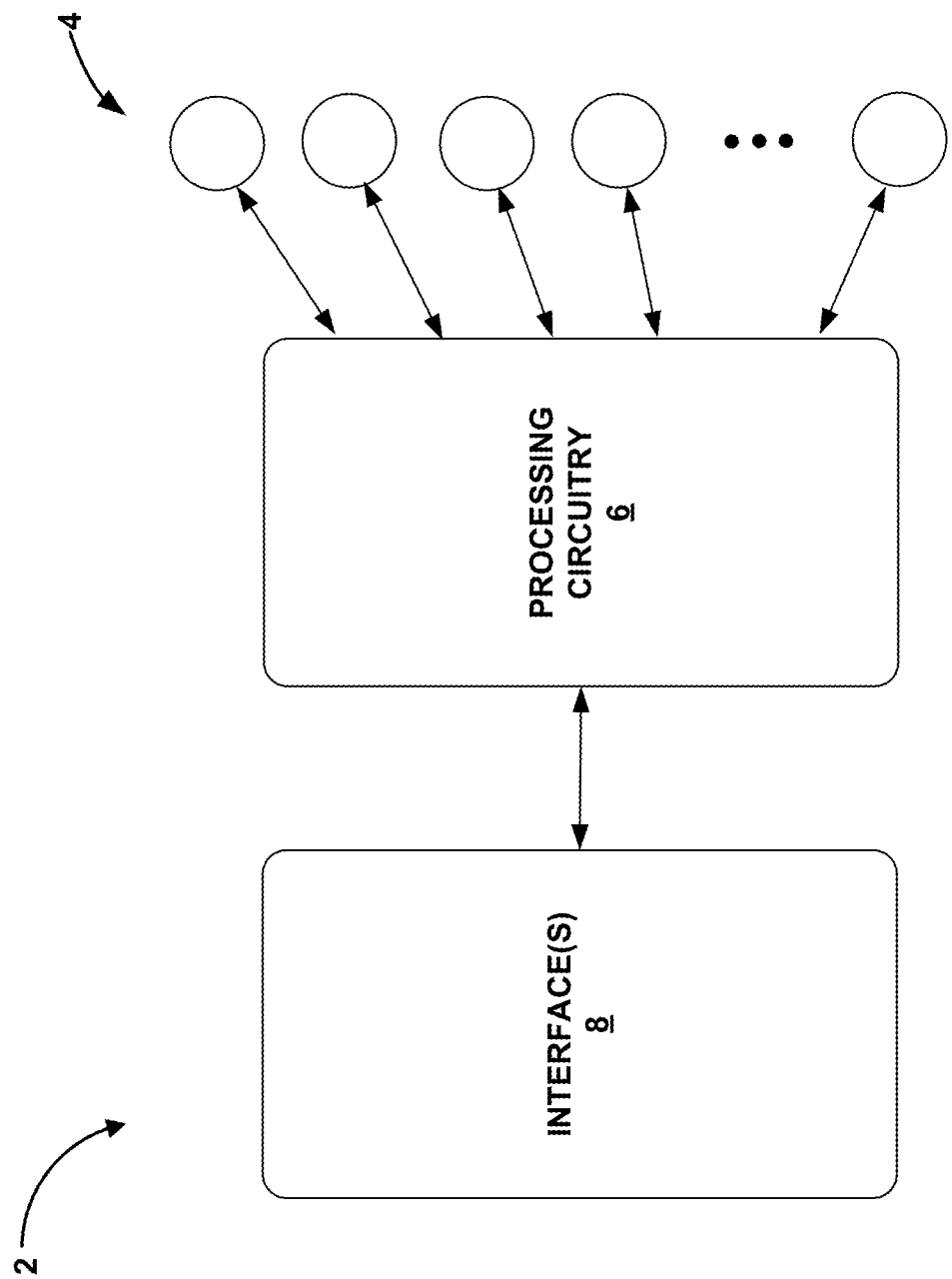
FIG. 1A is a block diagram illustrating an example system configured for detection and localization of MI according to the techniques of this disclosure.

FIG. 1A is a block diagram illustrating an example system 2 configured for detection and localization of MI according to the techniques of this disclosure. System 2 includes a set of electrodes 4 configured to be attached to a patient and to collect VCG signals according to the techniques of this disclosure. System 2 further comprises processing circuitry 6 configured to process the VCG signals using any of the techniques described herein, and based thereon to determine whether the patient has experienced MI and a location of the MI. System 2 may also include one or more interfaces 8. Interfaces 8 may include one or more user interfaces (e.g., for presenting the determinations regarding MI in the patient) and/or one or more communication interfaces (e.g., for providing the determinations regarding MI in the patient to one or more other devices in communication with system 2).

Using VCG instead of ECG signals may permit a better characterization of the heart electrical forces and the changes of them in the presence of MI. By characterizing the electrical forces of the heart via a 3D vector, VCG may facilitate identification of specific changes in the 3D vector associated to MI in different heart regions. Results can be observed from the table below:

| Research | Datasets | Methods | MI Detection Acc (%) | MI Detection Sens (%) | MI Detection Spec (%) | MI Location Acc (%) | MI Location Sens (%) | MI Location Spec (%) |
|---|---|---|---|---|---|---|---|---|
| [23] 2017 | 3 leads 3240 MI 3037 BC | Sample entropy, log energy entropy, and median slope; KNN/SVM | 81.71% | 79.01% | 79.26% | — | — | — |
| [21] 2017 | 1 lead 3222 MI 3055 BC | Shallow CNN with inception network | 84.64% | 85.33% | 84.00% | — | — | — |
| [24] 2019 | 12 leads 28213 MI 5373 BC | Energy entropy based on MODWPT; morphological features; SVM | 92.09% | 86.96% | 84.14% | — | — | — |
| [22] 2019 | 12 leads 53712 MI 10638 BC | CNN + BLSTM | 93.08% | 94.42% | 86.29% | — | — | — |
| [8] 2020 | 12 leads 28213 MI 5373 BC | ML-ResNet | 96.49% | 94.85% | 97.37% | 55.74% | 47.58% | 65.37% |
| Proposed | VCG 41311 MI 9930 BC | SGBM | 96.98% | 92.86% | 98.15% | 74.84% | 57.33% | 92.55% |

VCG may not normally be recorded in clinical practice. Therefore, it may be necessary to derive VCG from the ECG. Some transformations, such as Kors' and Dower's transforms, permit obtaining VCG from ECG signals. Research shows that MI detection performance is not affected when using VCG derived using Dower's transformation.

The PTB Diagnostics ECG database may be used to conduct research. This database contains 15 simultaneously recorded ECG signals (standard 12-lead ECG and three Frank orthogonal leads) from 290 subjects. The ECG signals are digitalized at 1000 samples per second. From all the available ECG signals, three Frank orthogonal leads (VCG) are used. The subjects in the PTB database are a mix representing different cardiac conditions together with healthy controls. Each subject is represented by one to five records. The records in the database are typically of 2 minutes duration and all the signals are recorded for at least 30 seconds.

From all the subjects available in the database, and for research purposes, the healthy control (HC) subjects (52 in total) and myocardial infarction (MI) subjects (148 in total) were selected. From the 148 MI subjects, one may be discarded due to excessive noise in the signals. In addition, another 21 MI subjects were discarded for not having annotations about MI location. The remaining MI subjects (126 in total) have different infarct locations as can be observed in Table 1. In addition, some of the MI locations have few subjects as to train and validate a model. For that reason, it may be decided to only consider those locations with more than 10 subjects (third column in Table 1), thus having at the end 112 MI subjects for the detection and location of MI.

TABLE 1

Number of subjects per infarct location in the PTB database

| MI Location | Number of Subjects | Included |
| --- | --- | --- |
| Inferior | 30 | Yes |
| Infero-posterior | 1 | No |
| Infero-postero-lateral | 8 | No |
| Infero-lateral | 23 | Yes |
| Anterior | 17 | Yes |
| Antero-septal | 26 | Yes |
| Antero-septo-lateral | 1 | No |
| Antero-lateral | 16 | Yes |
| Lateral | 1 | No |
| Posterior | 1 | No |
| Postero-lateral | 2 | No |

Figure 1B:
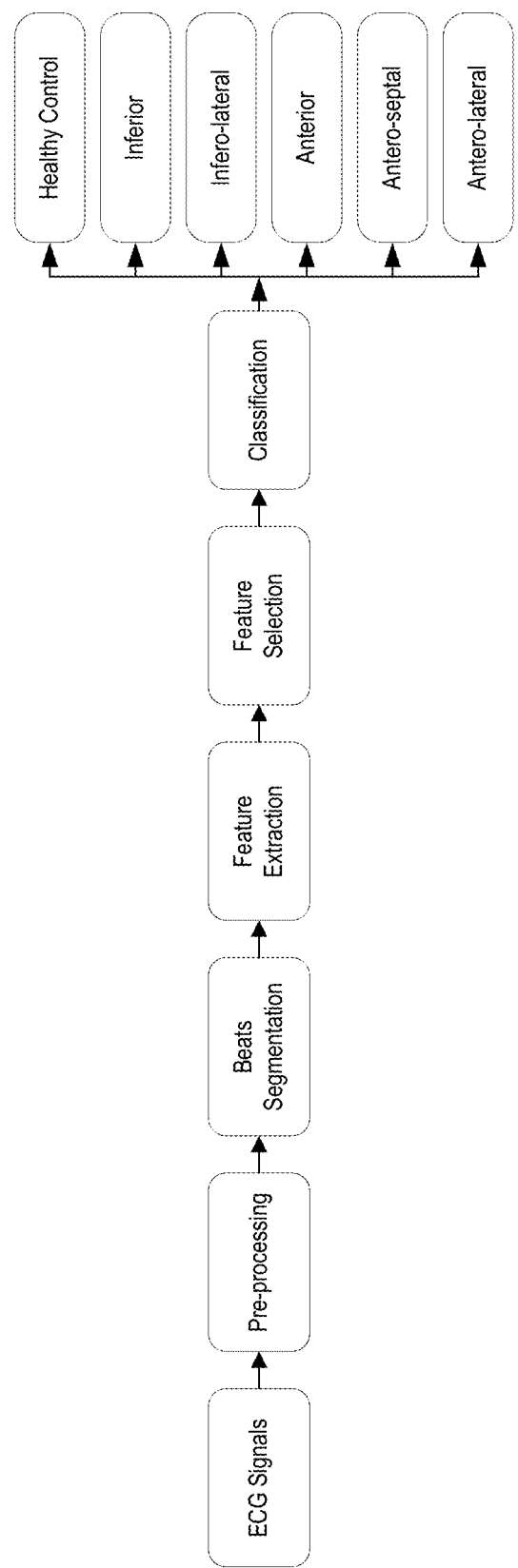
FIG. 1B is a block diagram of an example method for detection and location of MI, which may be implemented by processing circuitry of the system of FIG. 1A, in accordance with one or more embodiments.
Figure 2:
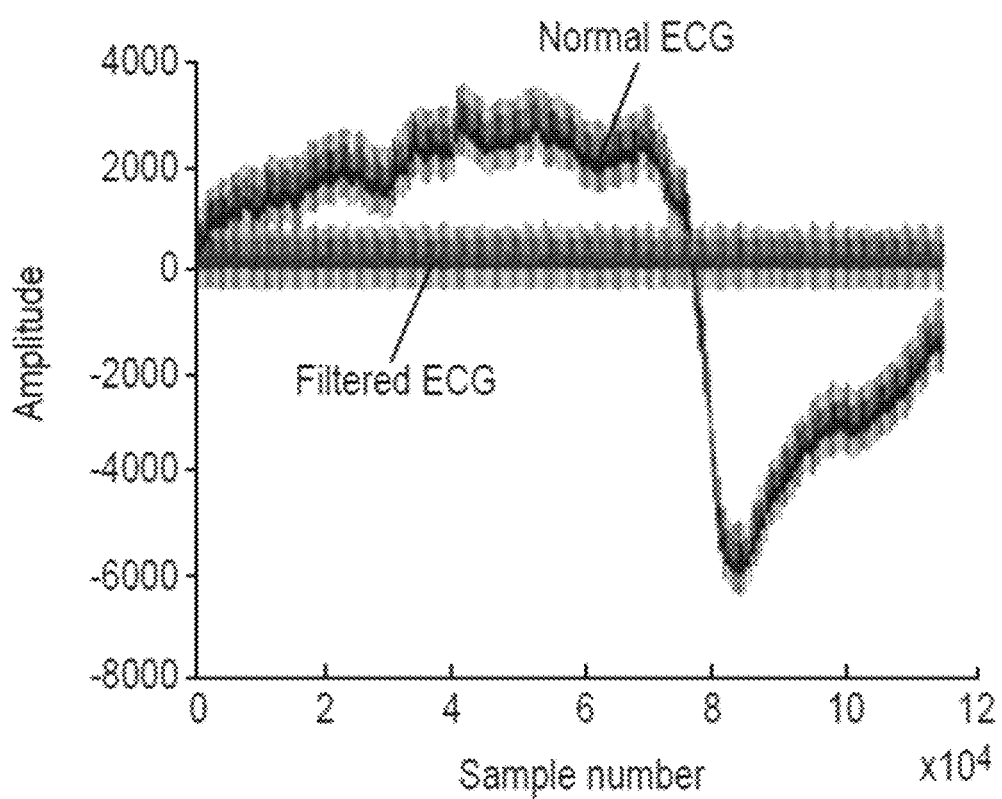
FIG. 2 is a chart of normal ECG signal with baseline wander together with filtered signal.

FIG. 1B illustrates a block diagram of a method for detection and location of MI, which may be implemented by processing circuitry 6 of system 2 of FIG. 1A. ECG signals may be pre-processed. For example, as shown in FIG. 2, ECG signals may be pre-processed to remove baseline wander, high frequency noise content, power line interference, etc. ECG signals may be pre-processed using a Butterworth filter with cut-off frequencies of approximately 0.8 Hz (e.g., to remove baseline wander) and approximately 40 Hz (e.g., to remove high frequency noise content and power line interference).

According to the example of FIG. 1B, the ECG signals may be segmented into individual cardiac beats, or portions thereof. Processing circuitry 6 may determine VCG signals from the pre-processed and segmented ECG signals. Processing circuitry 6 may extract and/or select features from the VCG signal segments. Processing circuitry 6 may determine a classification based on the features of one or more VCG signal segments. The classification may be MI or healthy. The classification may additionally or alternatively be healthy or one or more MI location classifications, such as inferior, infero-lateral, anterior, antero-septal, or antero-lateral.

Figure 3:
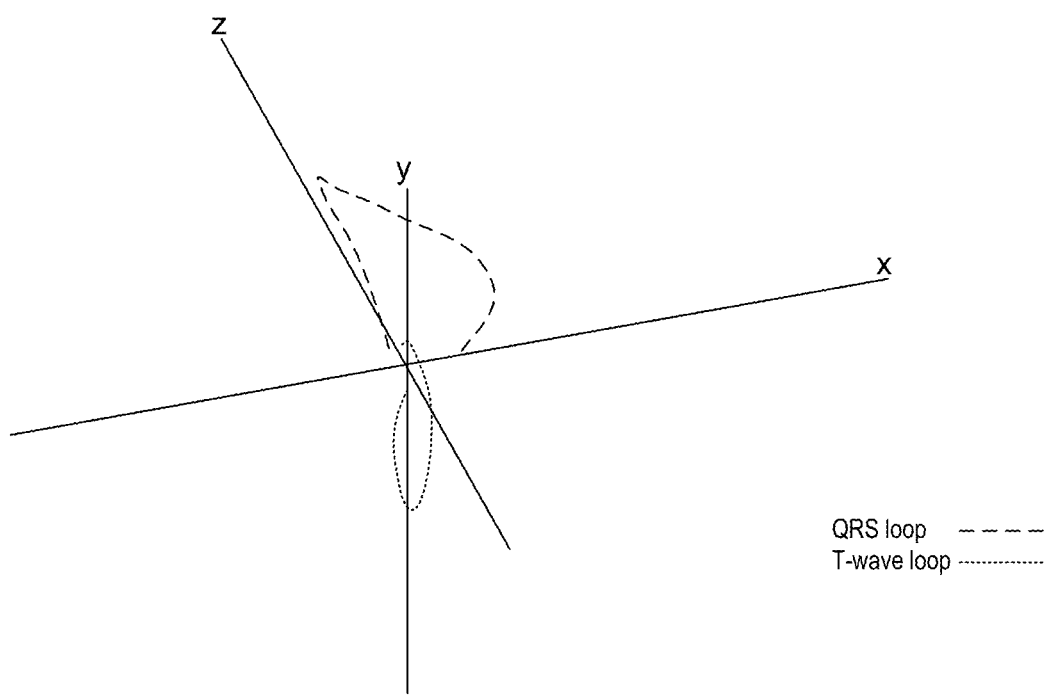
FIG. 3 is an example of a VCG signal with a QRS VCG loop and a T-wave VCG loop.

FIG. 3 shows a VCG signal. In particular, FIG. 3 is an example of QRS and T-wave VCG loops. The dashed line represents the QRS loop while the dotted line represents the T-wave loop. To detect and locate MI, a set of features may be derived from VCG loops. The set of features may be extracted for both QRS and T-wave complexes.

The generated VCG features can be categorized in two groups based on the information conveyed by the VCG features: geometrical features, which carry geometrical information about the VCG loops (e.g., size, morphology, location, orientation, etc.), and spatio-temporal features conveying spatial and temporal information (e.g., distribution on space, velocity of the loop, time spend in different regions, etc.).

Figure 4:
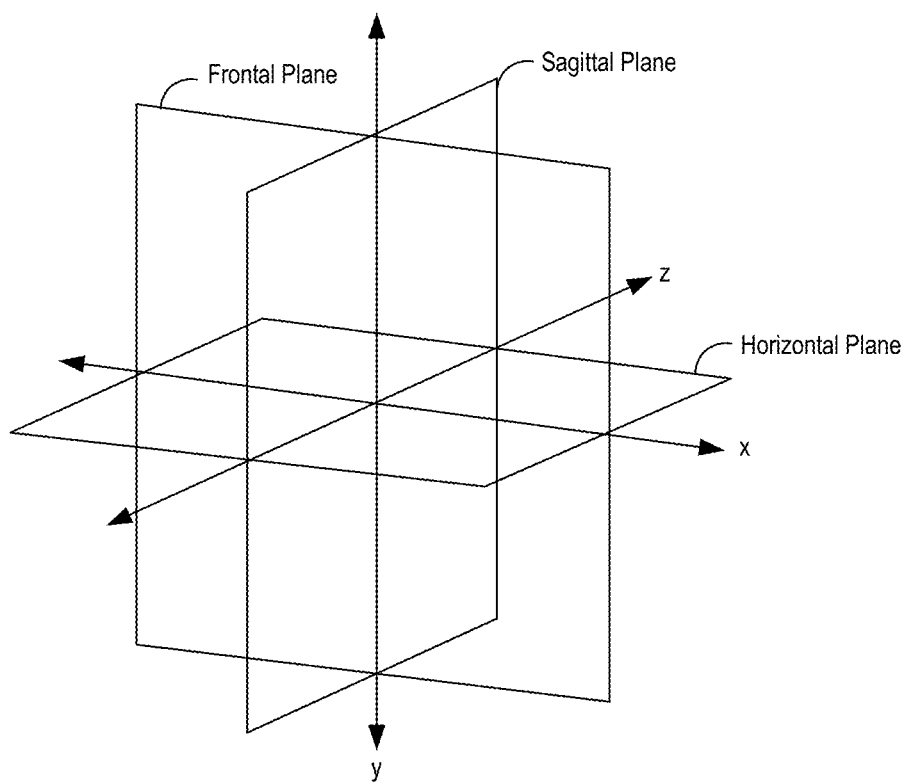
FIG. 4 is an illustration of coordinate system and reference planes, including the horizontal plane, frontal plane, and sagittal plane.

FIG. 4 illustrates a coordinate system and reference planes for the VCG loops. Geometrical features carry information about the geometrical properties (size, morphology, location, orientation, etc.) of VCG loops. For both QRS and T-wave VCG loops, a set of geometric features may be extracted, where the set may include one or more geometric features. Geometric features include, but are not limited to, loop perimeter, loop centroid, maximum vector length, loop area, Ratio Perimeter/Area, Maximum distance between centroid and VCG loop, Angle between Maximum vector length (MVL) and the different planes, Angle between QRS and T wave maximum vectors, and Angle between QRS and T wave optimal planes.

As an example, a method to detect and locate MI includes using geometrical features of VCG, including one or more of loop perimeter, loop centroid, maximum vector length, loop area, Ratio Perimeter/Area, Maximum distance between centroid and VCG loop, Angle between MVL and the different planes, Angle between QRS and T wave maximum vectors, and/or Angle between QRS and T wave optimal planes.

As used herein, loop perimeter refers to the loop's total length. Loop perimeter may be used to detect contour changes. The perimeter for the 3-dimensional loop may be computed as well as its projection in the horizontal, frontal and sagittal planes. FIG. 4 illustrates the horizontal, frontal and sagittal planes for the coordinate system described herein. In addition, the perimeter may be calculated for the X, Y and Z VCG components independently.

As used herein, loop centroid refers to an indication about the center of a heart's electrical forces. For example, the centroid of the loop may be computed using the following equation:

$$C = \frac{x_1 + x_2 + \ldots + x_n}{n}$$

where C is the centroid, $x_1, x_2, \ldots,$ and $x_n$ are the points composing the VCG loop, and n is the number of points composing the VCG loop. Centroid may be calculated for the three-dimensional loop as well as for its projection in the horizontal, frontal and sagittal planes (FIG. 4).

As used herein, a MVL refers to the maximum magnitude of heart's depolarization (QRS) and repolarization (T-wave). In order to calculate MVL (e.g., for every point of a loop), a vector may be constructed going from the origin of the VCG coordinate system (point [0, 0, 0]) to a specific loop point. From all those vectors, the one with the maximum magnitude may be selected. This may be done for the 3-dimensional loops as well as for its projection in the horizontal, frontal and sagittal planes. In addition, the same may be done for the X, Y and Z VCG components independently.

As used herein, loop area describes the total electric work performed by the heart during heart's depolarization and repolarization. The area of the loop may be computed by projecting the 3-dimensional loop into the best adjusted plane calculated using the least square method. In that case, the may be computed using the following equation:

$$A = \frac{1}{2} \sum_{i=1}^{n} (x_i y_{i+1} - x_{i+1} y_i)$$

where A is the area, i is the index of summation, n is the last value of the index of summation, $x_i$ is the x-coordinate value, and y, is the y-coordinate value.

In addition, the area may be computed for the X, Y and Z components ($A_x$, $A_y$ and $A_z$). Several combinations of those areas may be computed for the horizontal (XZ components), frontal (XY components) and sagittal planes (Y Z components), as well as a three-dimensional version combining the area of the X, Y and Z components as shown below:

$$A_{hp} = \sqrt{A_x^2 + A_z^2}$$

$$A_{fp} = \sqrt{A_x^2 + A_y^2}$$

$$A_{hp} = \sqrt{A_x^2 + A_z^2}$$

$$A_{sp} = \sqrt{A_y^2 + A_z^2}$$

$$A_{3d} = \sqrt{A_x^2 + A_z^2 + A_z^2}$$

where $A_{hp}$ is the area of the horizontal plane, $A_{fp}$ is the area of the frontal plane, $A_{sp}$ is the area of the sagittal plane, $A_{3d}$ is the area of the three-dimensional version combining the area of the X, Y and Z components, $A_x$ is the area of the X component, $A_y$ is the area of the Y component, and $A_z$ is the area of the Z component.

As used herein, ratio perimeter/area refers to the ratio between loop perimeter and area. The ratio perimeter/area may give an indication about loop morphology and about distribution of heart's electrical forces. Loops with the same area may have different perimeters and vice versa. Therefore, this parameter may help discriminating between loops.

As used herein, maximum distance between centroid and VCG loop refers to the maximum Euclidean distance between a loop's centroid and a point of the loop. While MVL describes the maximum magnitude of heart's depolarization and repolarization, the maximum distance from the centroid to the VCG loop may give an indication about the magnitude of depolarization and repolarization with respect to the center of the heart's electrical forces.

As used herein, the angle between MVL and the different planes refers to the angle between MVL and the frontal, horizontal and sagittal planes. The angle between MVL and the different planes may give an indication about the heart's electrical forces alignment with the frontal, horizontal and sagittal planes.

As used herein, the angle between QRS and T wave maximum vectors refers to the the angle between the maximum depolarization (QRS) and repolarization (T-wave) vector magnitudes. This parameter may indicate spatial alignment between depolarization and repolarization phases.

As used herein, the angle between QRS and T wave optimal planes refers to the angle between the best adjusted planes for both QRS and T-wave loops. This parameter may indicate spatial alignment between depolarization and repolarization phases.

Spatio-temporal features give information about the spatial and temporal distribution of the VCG loops in time and space. Octant features are a specific group of spatio-temporal features that result from dividing the space in octants and evaluate VCG loop properties in them. Table 2 shows the different octants as function of the values for X, Y and Z components.

TABLE 2

Octants numbering (FIG. ).

| Octant | XYZ | Location |
|---|---|---|
| 1 | − − − | Right-Superior-Anterior |
| 2 | − − + | Right-Superior-Posterior |
| 3 | − + − | Right-Inferior-Anterior |
| 4 | − + + | Right-Inferior-Posterior |
| 5 | + − − | Left-Superior-Anterior |
| 6 | + − + | Left-Superior-Posterior |
| 7 | + + − | Left-Inferior-Anterior |
| 8 | + + + | Left-Inferior-Posterior |

A set of one or more octant features for both QRS and T-wave loops may be calculated. Octant features may include, but are not limited to, octant average vector length, MVL per octant, percentage of time per octant, variance of vector magnitude per octant, etc.

As used herein, octant average vector length refers to the average vector length in the different octants. This feature may indicate how heart's electrical forces are distributed in space.

As used herein, MVL per octant refers to the MVL of the loop in the different octants. This feature may indicate the maximum magnitude of heart's depolarization and repolarization in the octants.

As used herein, percentage of time per octant refers to the percentage of time that the loop spends in the different octants. This feature may indicate the time distribution of the heart's electrical forces in the different octants.

As used herein, variance of vector magnitude per octant refers to the variance of the loop in the different octants. This feature may indicate information about dispersion (or alignment if taking the inverse of it) during depolarization and repolarization in the different octants.

Machine learning may be used to assess MI locations using ECG. In some examples, a ML-ResNet deep learning model and an inter-patient scheme may be used. As deep learning models may need large amounts of data in order to learn superficial representations of their target classes, GBM, which is a less complex approach, may be used in some examples to solve the MI detection and location problems using ECG signals and an inter-patient scheme. GBM has less complexity than deep learning models and thus can generalize better with less data.

A test was conducted to evaluate the efficacy of a GBM model. A total of 52 healthy control (HC) and 112 myocardial infarct (MI) subjects were considered in analysis. Subjects in both groups were randomly split between training and test datasets using the classic 80/20 criteria. The training dataset was used to build and train the GBM model. To ensure generalization in results, 10-fold cross-validation was used during the training phase for model hyperparameter tuning.

Table 3 shows subjects' distribution around the different categories as well as the number of cardiac beats available for each class.

TABLE 3

Subjects and cardiac beat distributions between training and test datasets.

| Subject Class | Training Subjects | Training Beats | Test Subjects | Test Beats |
|---|---|---|---|---|
| MI Inferior | 24 | 9124 | 6 | 2180 |
| MI Infero-lateral | 18 | 6230 | 5 | 1330 |
| MI Anterior | 14 | 4631 | 3 | 1235 |
| MI Antero-septal | 21 | 8243 | 5 | 2404 |
| MI Antero-lateral | 13 | 5057 | 3 | 857 |
| Healthy Control | 42 | 7648 | 10 | 2282 |

To evaluate the method's performance, a two-step approach was followed. First, the method's capabilities were evaluated to solve the detection problem, i.e., to discriminate MI from HC condition. Second, performance to differentiate between all the different classes depicted in table 3 was analyzed. In both cases, an inter-patient scheme was used. Results on both steps are detailed in (MI Detection) and (MI Location).

As discussed below, for the MI detection problem, a GBM model was trained to discriminate MI from HC subjects. All MI subjects were aggregated independently of the location into a unique MI group and compared against HC subjects. Table 4 shows the subjects' distributions of the two categories for both, training and test datasets.

TABLE 4

Subjects and caridac beat distributions to solve the detection problem.

| Subject Class | Training Subjects | Training Beats | Test Subjects | Test Beats |
|---|---|---|---|---|
| MI | 90 | 33305 | 22 | 8006 |
| Healthy Control | 42 | 7648 | 10 | 2282 |

With the training subjects, a GBM model was trained (as implemented in the gbm R package) to discriminate between HC and MI subjects. As mentioned earlier, 20% of the patients were reserved as an independent test dataset. For the MI detection method, the accuracy in the test dataset was 96.98%, having a sensitivity of 92.86% and a specificity of 98.15% (table 5).

TABLE 5

Method MI detection performance using an inter-patient scheme.

| | Acc (%) | Sens (%) | Spec (%) |
|---|---|---|---|
| MI vs HC | 96.98 | 92.86 | 98.15 |

Figure 5:
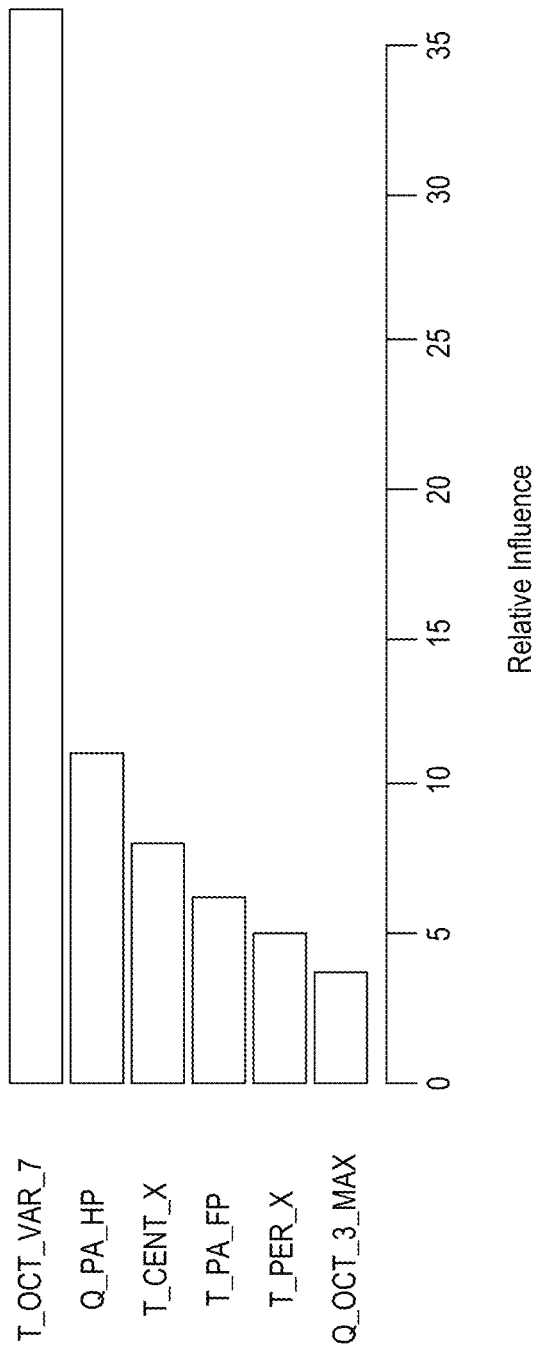
FIG. 5 is chart illustrating relative influence of features for MI detection.

GBM models advantageously ranks features according to their relative influence in the decision-making process. This is very useful because it allows extraction of information about the relevant features driving decisions in the model. For the MI detection case, FIG. 5 shows the six most influential features, while table 6 contains those features' description.

TABLE 6

Best six features for MI detection.

| Feature | Description |
|---|---|
| T_OCT_7_VAR | Variance in octant 7 during the T-wave loop. |
| Q_PA_HP | Ratio between the perimeter and the area of the QRS-loop projection in the horizontal plane. |
| T_CENT_X | X component of the centroid of the T-wave loop. |
| T_PA_FP | Ratio between the perimeter and the area of the T-wave-loop projection in the frontal plane. |
| T_PER_X | Curve length of X component of the T-wave loop. |
| Q_OCT_8_MAX | Maximum vector length of the QRS-loop in octant 3. |

Figure 6:
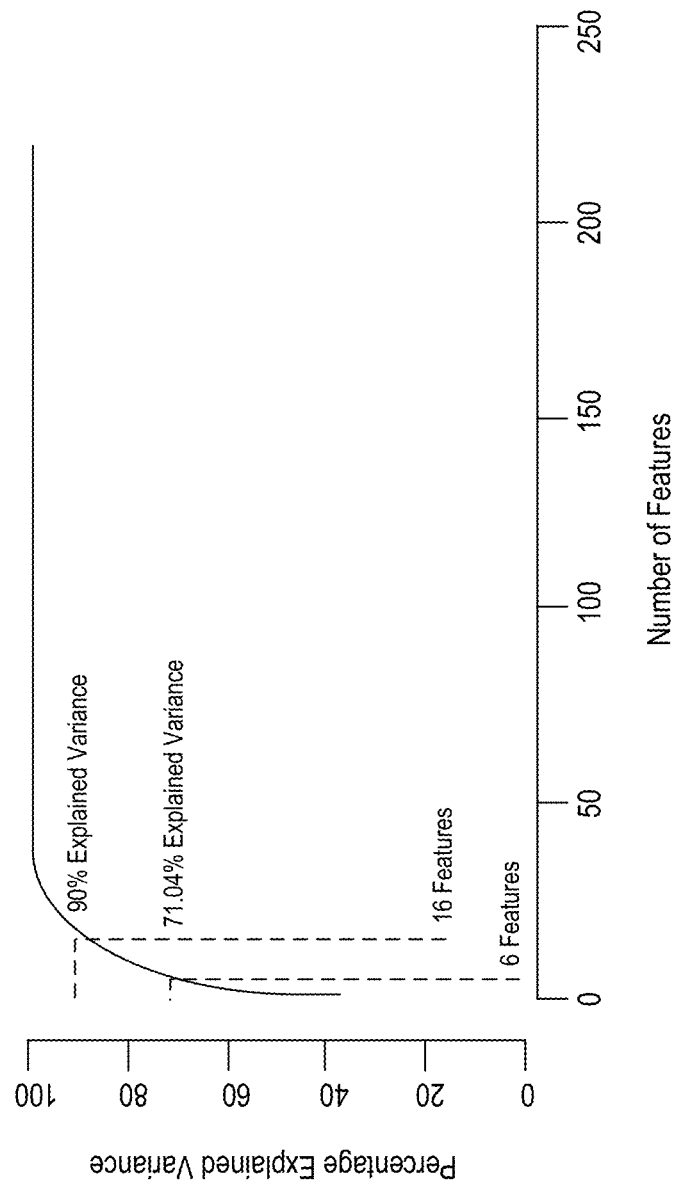
FIG. 6 is a chart illustrating variance as a function of the number of features included in a model for detection of MI.

FIG. 6 shows the percentage of variance explained by the model as function of the number of features included in it. With the six most relevant features depicted in FIG. 5, 71.04% of the variance associated to the MI detection problem was captured. Also, another 10 features were needed to explain 90% of the variance (FIG. 6).

Figure 7:
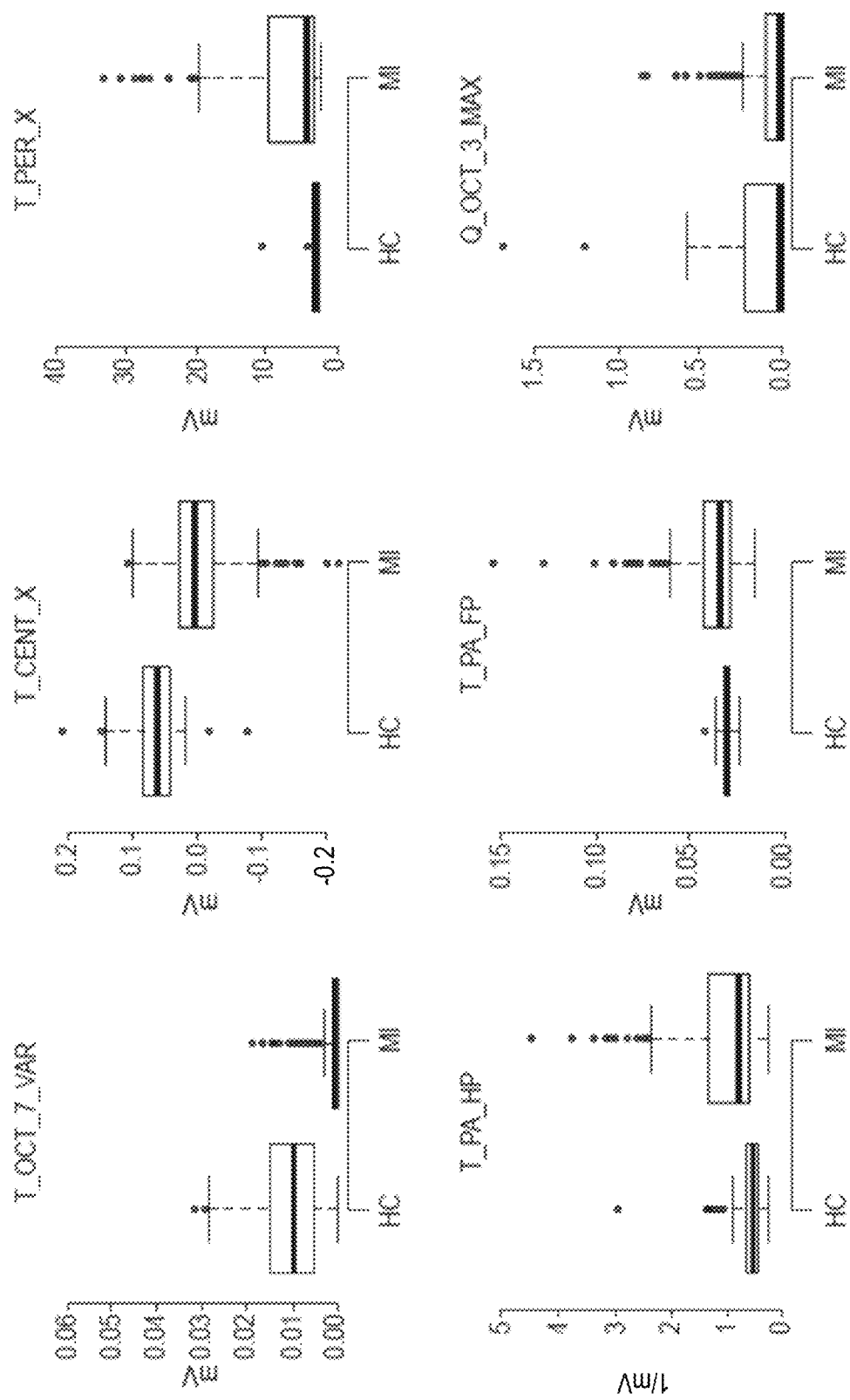
FIG. 7 includes boxplots with values of influential features for MI detection.

FIG. 7 shows boxplots with the values of the six relevant features for the HC and MI cases. Those features includes T_OCT_7_VAR, Q_PA_HP, T_CENT_X, T_PA_FP, T_PER_X, and Q_OCT_3_MAX.

For the MI location problem, a GBM model was trained to discriminate between all the different categories depicted in table 3. As in the MI detection problem, GBM as implemented in the gbm R package was used. A multinomial distribution to train the model and 10-fold cross-validation for hyperparameter fine tuning was used. Table 7 shows the confusion matrix for the different groups as well as the accuracy, sensitivity and specificity. As used herein, MI-IL refers to MI in the infero-lateral location, MI-A refers to MI in the anterior 235 location, MI-AS refers to MI in the antero-septal location, MI-I refers to MI in the inferior location, MI-AL refers to MI in the antero-lateral location and HC refers to the healthy control group without MI. As can be observed in table 7, the mean MI location accuracy is 74.94% while sensitivity and specificity are 57.33% and 92.55% respectively.

TABLE 7

Confusion matrix for MI detection and location on inter-patient scheme.

| | Predicted | | | | | | | | |
|---|---|---|---|---|---|---|---|---|---|
| | MI-IL | MI-A | MI-AS | MI-I | MI-AL | HC | Acc (%) | Sens (%) | Spec (%) |
| MI-IL | 541 | 166 | 132 | 375 | 116 | 163 | 68.33 | 40.67 | 95.98 |
| MI-A | 0 | 409 | 228 | 285 | 313 | 0 | 61.40 | 33.12 | 89.67 |
| MI-AS | 0 | 360 | 1716 | 0 | 328 | 0 | 80.97 | 71.38 | 90.55 |

TABLE 7-continued

Confusion matrix for MI detection and location on inter-patient scheme.

|  | Predicted | | | | | | | | |
| --- | --- | --- | --- | --- | --- | --- | --- | --- | --- |
|  | MI-IL | MI-A | MI-AS | MI-I | MI-AL | HC | Acc (%) | Sens (%) | Spec (%) |
| MI-A | 31 | 409 | 256 | 1336 | 0 | 148 | 75.12 | 61.28 | 88.96 |
| MI-AL | 166 | 0 | 129 | 146 | 416 | 0 | 70.26 | 48.54 | 91.97 |
| HC | 163 | 0 | 0 | 89 | 0 | 2030 | 93.55 | 88.96 | 98.15 |
| Means | — | — | — | — | — | — | 74.94 | 57.33 | 92.55 |

Figure 8:
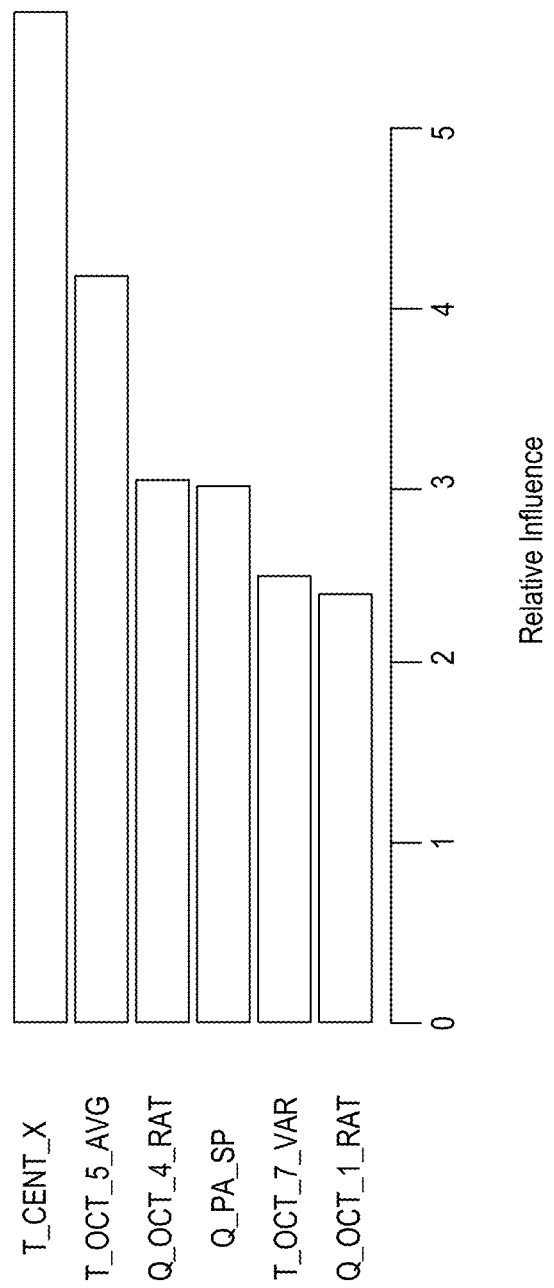
FIG. 8 is a chart illustrating relative influence features for MI location.

FIG. 8 shows the six most influential features for MI location, while table 8 contains those features' description. As for the MI detection case, six features were chosen only for explanation purposes.

TABLE 8

Best six features for MI location.

| Feature | Description |
| --- | --- |
| T_CENT_X | X component of the centroid of the T-wave loop. |
| T_OCT_5_AVG | Average vector magnitude in octant 5 during the T-wave loop. |
| Q_OCT_4_RAT | Average time spend by the QRS-loop in octant 4. |
| Q_PA_SP | Ratio between the perimeter and the area of the QRS-loop projection in the sagittal plane. |
| T_OCT_7_VAR | Variance in octant 7 during the T-wave loop. |
| Q_OCT_1_RAT | Average time spend by the QRS-loop in octant 1. |

Figure 9:
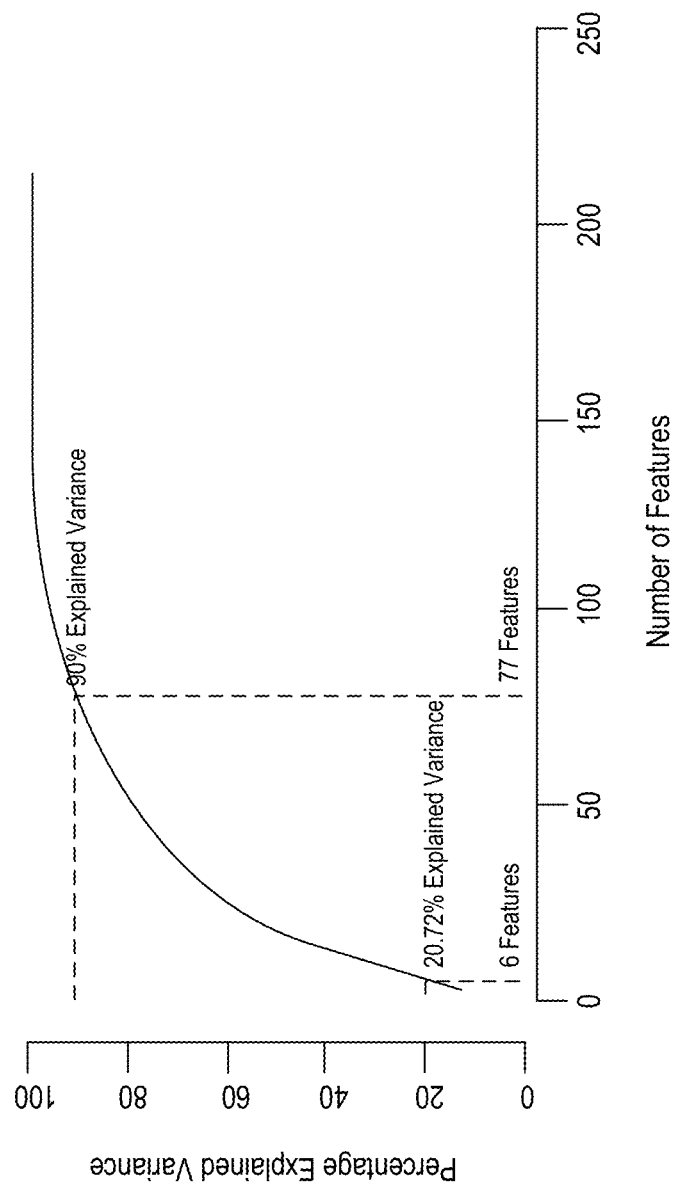
FIG. 9 is a chart of percentage of explained variance as function of the number of features included in a model for determining location of MI.

Referring to FIG. 9, this time, six features only captured 20.72% of the variance. The reason is that, for the MI location problem, the decision-making process is more complex (there are more classes and not just MI vs HC), and therefore more features may be needed in order to capture a reasonable amount of variance. For example, 77 features were needed for 90% of the variance associated with the problem to be captured. FIG. 9 is a percentage of explained variance as function of the number of features included in the model for the MI location problem.

Figure 10:
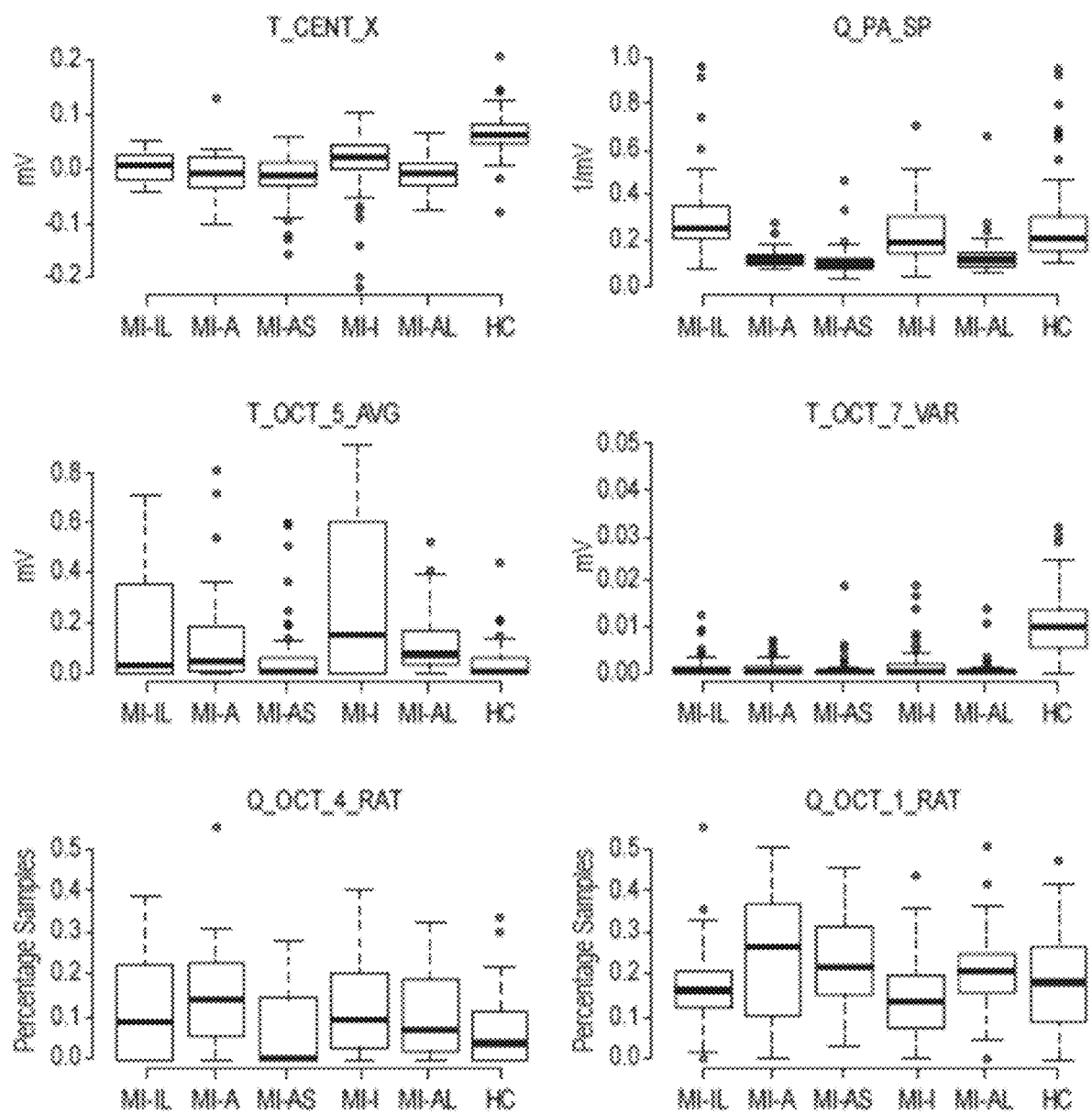
FIG. 10 includes boxplots with values of six influential features for MI location.

FIG. 10 shows boxplots with the values of the best six features for the different categories. There are some features that can separate one class from the rest, such as T_OCT_7_VAR (which separates HC from the rest). Also, there are other features able to separate two or more classes from the rest, such as, for example, Q_PA_SP and Q_OCT_1_RAT.

VCG may provide information on spatial propagation and orientation of heart's electrical forces. This may be crucial to assess the presence and location of MI. In addition, the system may include an inter-patient approach in the validation of the methods. Prior art approaches use an intra-patient approach which can lead to overoptimistic results and may not properly reflect real performance. As an example, for the MI detection problem using ECG signals, five studies were found that used an inter-patient scheme. Table 9 shows a performance comparison of those five studies. As can be observed from Table 9, the method disclosed herein had the best accuracy (96.98%) and specificity (98.15%).

Deep learning models are complex and may in turn need big amounts of data to be properly trained. GBM models are less complex and may have a lower number of hyperparameters to be tuned than CNN. Accordingly, improvements in performance may be due to both better model generalization (simpler model) and a more suitable set of features (VCG).

| Research | Datasets | Methods | MI Detection | | | MI Location | | |
| --- | --- | --- | --- | --- | --- | --- | --- | --- |
|  |  |  | Acc (%) | Sens (%) | Spec (%) | Acc (%) | Sens (%) | Spec (%) |
| [23] 2017 | 3 leads 3240 MI 3037 BC | Sample entropy, log energy entropy, and median slope; KNN/SVM | 81.71% | 79.01% | 79.26% | — | — | — |
| [21] 2017 | 1 lead 3222 MI 3055 BC | Shallow CNN with inception network | 84.64% | 85.33% | 84.00% | — | — | — |
| [24] 2019 | 12 leads 28213 MI 5373 BC | Energy entropy based on MODWPT; morphological features; SVM | 92.09% | 86.96% | 84.14% | — | — | — |
| [22] 2019 | 12 leads 53712 MI 10638 BC | CNN + BLSTM | 93.08% | 94.42% | 86.29% | — | — | — |
| [8] 2020 | 12 leads 28213 MI 5373 BC | ML-ResNet | 96.49% | 94.85% | 97.37% | 55.74% | 47.58% | 65.37% |
| Proposed | VCG 41311 MI 9930 BC | SGBM | 96.98% | 92.86% | 98.15% | 74.84% | 57.33% | 92.55% |

When comparing the MI detection and MI location problems in terms of complexity, the latter is a more complex problem. In order to quantify that complexity, a criteria, such as the following equation, may be used. It should be understood that the following equation is only an example and that the criteria may depend on the problem, the model approach, the nature of the features used, To ensure a proper comparison, the parameters may need to be the same for the MI detection and MI location problems.

$$\text{Problem Complexity} = \frac{\text{\# of features to explain 90\% of variance}}{\text{Total \# of features}}$$

Figure 11:
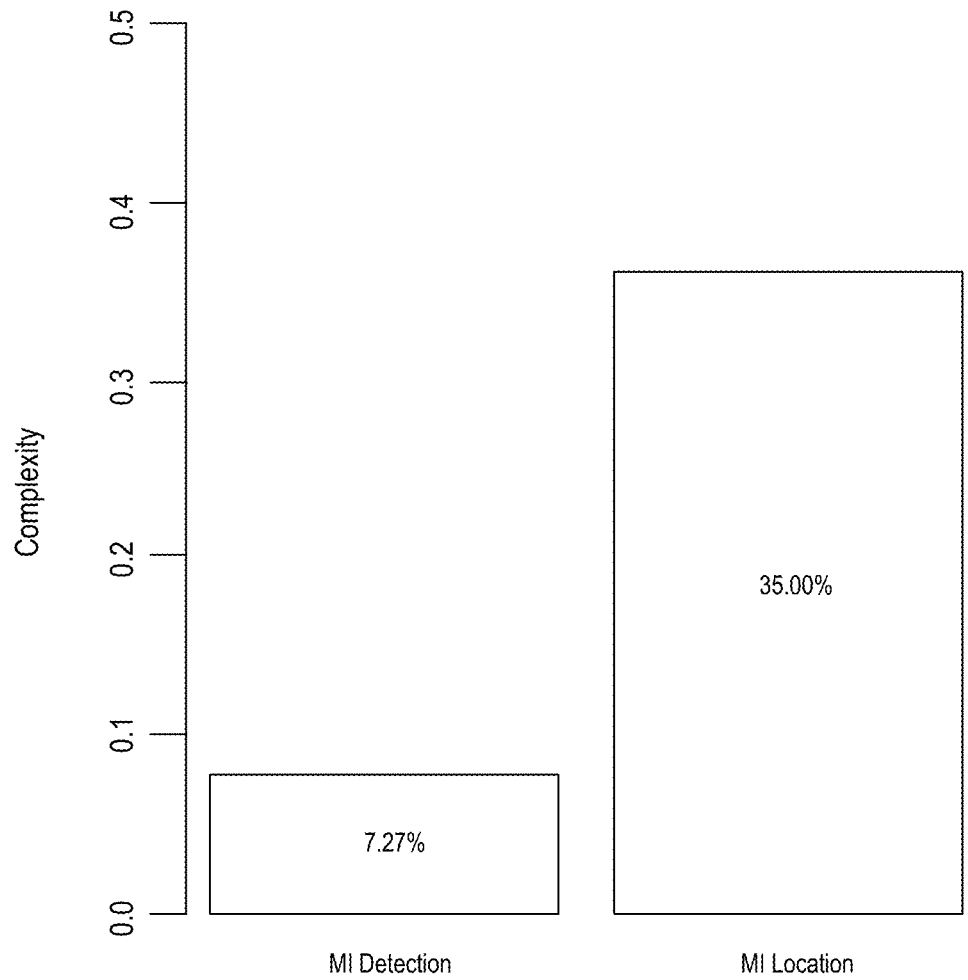
FIG. 11 illustrates a complexity comparison between MI detection and MI location.

As shown in FIG. 6, for the MI detection problem, 16 features were needed to explain 90% of the variance, while, as shown in FIG. 9, for the MI location problem, 77 features were needed. FIG. 11 shows the complexity comparison (as defined above) between the MI detection and MI location problems. The MI location problem is around 4.8 times more complex than the MI location one. This increased complexity in the MI location problem explains the drop in the model performance observe in table 9. Specifically, more data may be needed in order to effectively perform more complex tasks.

Figure 12:
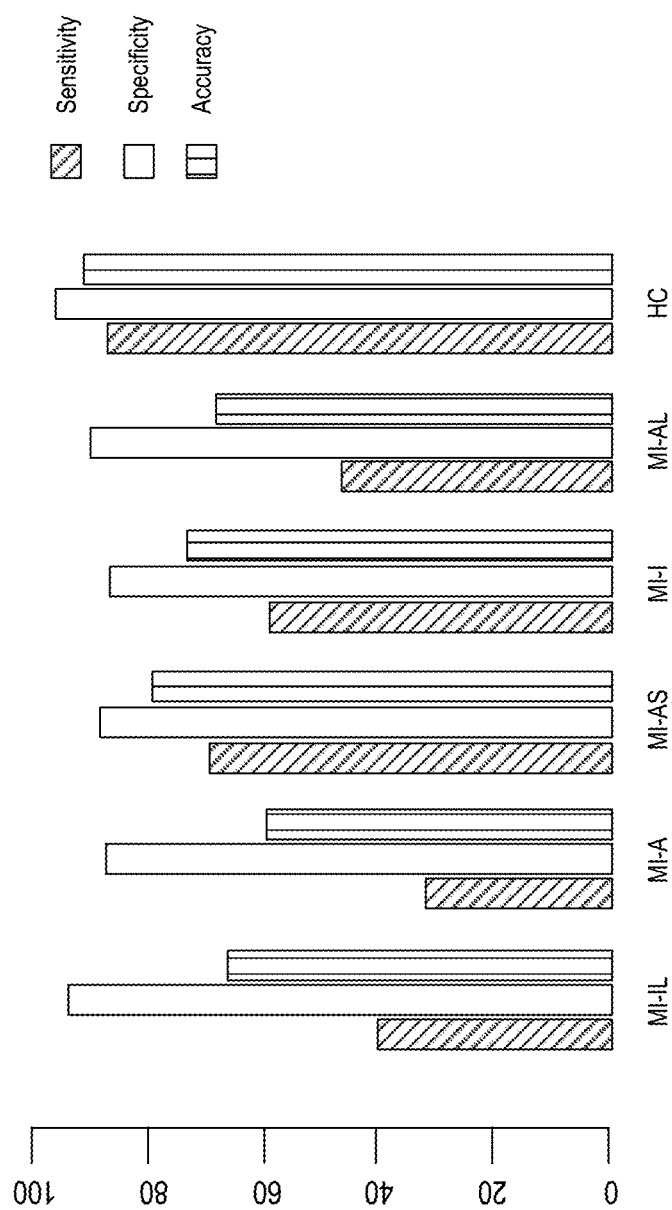
FIG. 12 illustrates MI location performance per class.

For the MI location problem, performance may not be the same for all the classes. FIG. 12 shows MI location performance for the method described herein per class. The method's specificity was above 88% in all cases. The method's accuracy was above 70% in four of the six cases and never below 60%.

Referring to FIG. 12, sensitivity was greatest for HC. For MI subjects, the antero-septal location was the one showing the highest sensitivity (71.38%) followed by the inferior location (61.28%). For the antero-lateral, anterior and infero-lateral locations, the sensitivity of method was below 50%. The decrease in sensitivity may be due to: (i) the Frank's 3-lead VCG system, (ii) the set of features derived from the VCG or (iii) the number of subjects available for the different classes.

Figure 13A:
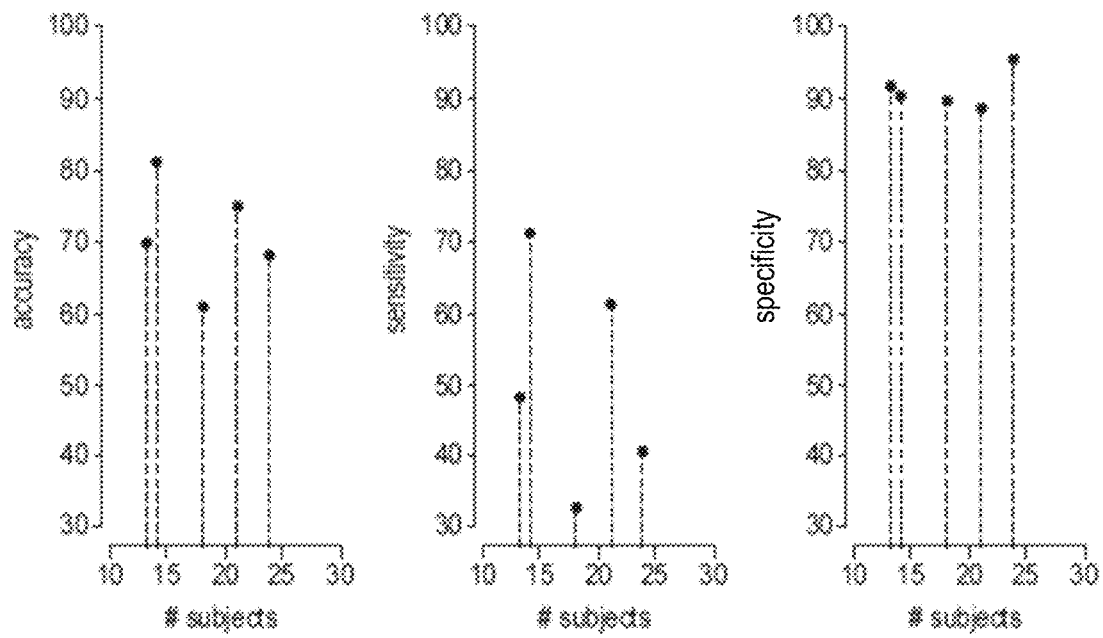
FIG. 13A illustrates charts that show performance versus number of subjects used for training a model for detection/location of MI.
Figure 13B:
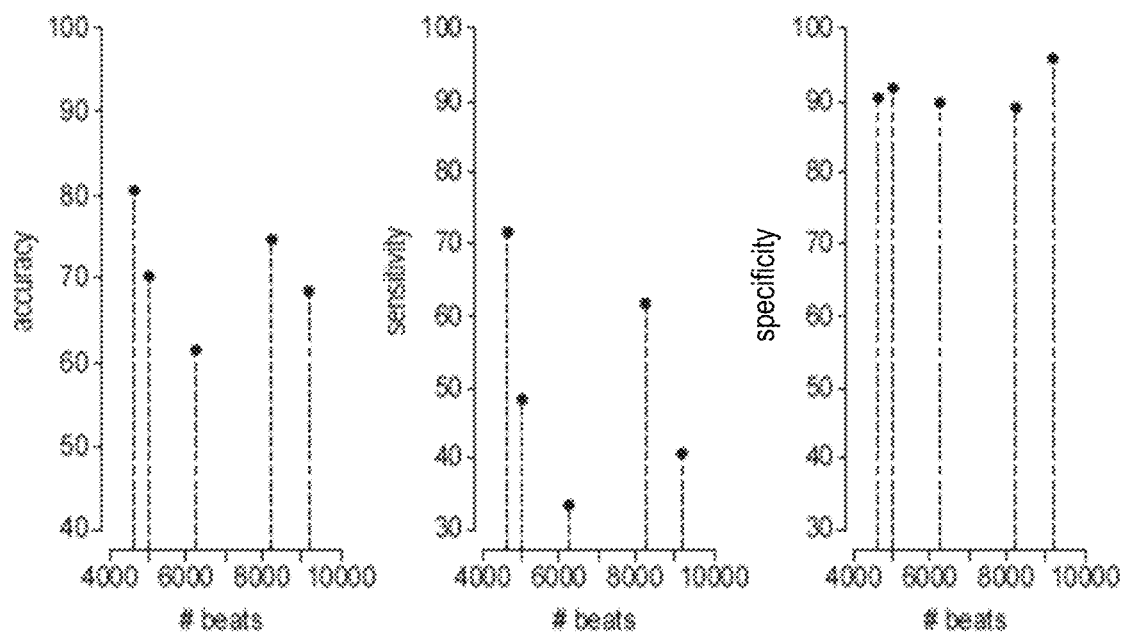
FIG. 13B illustrates charts that show performance versus number of cardiac beats used for training a model for detection/location of MI.

FIG. 13A shows accuracy, sensitivity and specificity against the number of subjects available during the training phase for each MI location (see table 3), and FIG. 13B shows accuracy, sensitivity and specificity against number of cardiac beats available during the training phase for each MI location. From FIGS. 13A-B, there appears to be no relation between the number of subjects or cardiac beats and the performance of the method.

Compared to deep learning models, GBM models may be more generalizable and easier to interpret. With GBM models, one can identify the different features involved in the decision-making process, as well as how they relate to the ischemic process. For example, when analyzing the six best features for the MI detection and MI location problems, features T CENT X and T OCT 7 VAR were common to both problems. Those features are known to be well-suited for separating HC subjects from MI subjects, explaining their appearance in both problems.

In addition, the more common manifestations of AMI (in absence of LVH and LBBB) are related to changes in heart's repolarization and those features are related to the T-wave. With respect to the T CENT X feature, for HC subjects, the T-wave loop centroid is located in the positive X axis (FIG. 7), while for the MI subjects it is displaced towards 0 and negative values. For T OCT 7 VAR, the variance in octant 7 (FIG. 4) is higher for HC subjects, while for MI subjects it is small. A clinician may interpret this information to conclude that in HC subjects, the T-wave loop trajectories are bigger in octant 7. Analyzing all the selected features and its relation to physiology is beyond the scope of this work. Nonetheless, the method permits a high degree of explainability as well as other advantages described in this disclosure.

FIG. 15 illustrates a flow diagram of an example method for detecting and localizing MI in accordance with techniques of this disclosure. The example method may be performed by system 2 of FIG. 1A, or any other system configured to receive ECG or VCG signals.

According to the example of FIG. 14, ECG signals of a patient are sensed via electrodes 4 (100). Processing circuitry 6 determines VCG signals as a function of the ECG signals, such as features from VCG signal segments, as described herein (102). Processing circuitry 6 determines whether MI is detected based on the VCG features (104). In the absence of MI (N of 104), processing circuitry 6 may process different VCG segments (100-104). If MI is detected (Y of 104), processing circuitry 6 may determine a location of the MI based on the VCG segments (106). Processing circuitry 6 may provide an indication of MI and MI location via interfaces 8.

A novel method for the detection and location of MI is disclosed herein. A set of VCG features is computed from the PTB diagnostic ECG database. Using these features, two GBM models were built, one of the detection of MI and another one for MI location. To validate the method, an inter-patient scheme may be used in order to have more realistic and less overoptimistic results. The proposed method performs better than other prior methods using an inter-patient scheme, especially for the MI location problem. For MI detection sensitivity, specificity and accuracy were 92.86%, 98.15% and 96.98% respectively. For the MI location, the average sensitivity, specificity and accuracy among classes were 57.33%, 92.55% and 74.84% respectively. The method, contrary to other proposed methods, has certain degree of explainability. Also, physiological knowledge can be derived from the features used in the decision-making process.

The methods/systems will include features targeted to increase sensitivity. Also, to increase sample data size by including other ECG datasets with labelled data. There is a growing need for new ECG datasets that contain a large number of patients with labelled data for the automated detection and location of MI.

In this way, various aspects of the techniques may enable the following examples.

Example 1: A method includes detecting whether one or more myocardial infarctions (MI) has occurred using vectorcardiographic (VCG) signals with gradient boosting, the VCG signals including VCG loops; and determining an MI location using the VCG signals with gradient boosting if one or more myocardial infarctions are detected.

Example 2: The method of example 1, wherein determining the MI location includes identifying a region of a heart of where the one or more MI has occurred.

Example 3: The method of any one of examples 1 or 2, wherein determining the MI location includes using geometrical features of VCG.

Example 4: The method of example 3, wherein the geometrical features include one or more of loop perimeter, loop centroid, maximum vector length, loop area, Ratio Perimeter/Area, Maximum distance between centroid and VCG loop, Angle between MVL and the different planes, Angle between QRS and T wave maximum vectors, and/or Angle between QRS and T wave optimal planes.

Example 5: The method of any one of examples 3 or 4, wherein using geometrical features of VCG includes using geometrical features of QRS VCG loops and T-wave VCG loops.

Example 6: The method of example 5, further comprising using the geometrical features of QRS VCG loops and T-wave VCG loops with the gradient boosting.

Example 7: The method of any one of examples 1-6, wherein determining the MI location includes obtaining spatio-temporal distribution information of the VCG loops.

Example 8: The method of example 7, wherein obtaining spatio-temporal distribution information includes computing octant average vector length, MVL per octant, percentage of time per octant, and/or variance of vector magnitude per octant.

Example 9: The method of any one of examples 7 or 8, wherein obtaining spatio-temporal distribution information of the VCG loops includes obtaining spatio-temporal distribution information of the VCG loops for both QRS VCG loops and T-wave VCG loops.

Example 10: The method of example 9, further comprising using the spatio-temporal distribution information of the QRS VCG loops and T-wave VCG loops with the gradient boosting.

Example 11: A system includes a set of electrodes configured to sense vectorcardiographic (VCG) signals; and processing circuitry configured to: detect whether one or more myocardial infarctions (MI) has occurred using the VCG signals with gradient boosting; and determine a MI location using the VCG signals and gradient boosting.

Example 12: The system of example 11, wherein the determination of the MI location includes identification of a region of a heart of where the one or more MI has occurred.

Example 13: The system of any one of examples 11 or 12, wherein the determination of the MI location includes use of VCG geometrical features.

Example 14: The system of example 13, wherein the determination of the MI location including use VCG geometrical includes using geometrical features of QRS VCG loops and T-wave VCG loops.

Example 15: The system of example 14, further comprising using the geometrical features of QRS VCG loops and T-wave VCG loops with the gradient boosting.

Example 16: The system of any one of examples 13-15, wherein the geometrical features include one or more of loop perimeter, loop centroid, maximum vector length, loop area, Ratio Perimeter/Area, Maximum distance between centroid and VCG loop, Angle between MVL and the different planes, Angle between QRS and T wave maximum vectors, and/or Angle between QRS and T wave optimal planes.

Example 17: The system of any one of examples 11-16, wherein the determination of the MI location includes spatio-temporal distribution information of the VCG loops.

Example 18: The system of example 17, wherein obtaining spatio-temporal distribution information includes computing octant average vector length, MVL per octant, percentage of time per octant, and/or variance of vector magnitude per octant.

Example 19: The system of any one of examples 17 or 18, wherein obtaining spatio-temporal distribution information of the VCG loops includes obtaining spatio-temporal distribution information of the VCG loops for both QRS VCG loops and T-wave VCG loops.

Example 20: The system of example 19, further comprising using the spatio-temporal distribution information of the QRS VCG loops and T-wave VCG loops with the gradient boosting.

Any combination of detection and location of heart failure is contemplated. These and other examples are within the scope of the following claims.

The invention claimed is:

1. A method comprising:
    detecting electrocardiogram (ECG) signals from a patient;
    determining vectorcardiographic (VCG) signals as a function of the ECG signals, wherein the VCG signals comprise VCG loops;
    extracting features from the VCG signals, wherein the extracted features comprise at least one of geometrical features of the VCG loops and/or spatio-temporal information of the VCG loops;
    detecting, using one or more trained machine learning models, one or more myocardial infarctions (MI) based on the extracted features; and
    determining, using the one or more trained machine learning models, an MI location of the detected one or more myocardial infarctions based on the extracted features.

2. The method of claim 1, wherein determining the MI location includes identifying a region of a heart of where the one or more MI has occurred.

3. The method of claim 1, wherein the geometrical features include one or more of loop perimeter, loop centroid, maximum vector length (MVL), loop area, Ratio Perimeter/Area, Maximum distance between centroid and VCG loop, Angle between MVL and the different planes, Angle between QRS and T wave maximum vectors, or Angle between QRS and T wave optimal planes.

4. The method of claim 1, wherein the geometrical features of the VCG loops includes geometrical features of QRS VCG loops and T-wave VCG loops.

5. The method of claim 1, wherein the spatio-temporal information includes one or more of octant average vector length, maximum vector length (MVL) per octant, percentage of time per octant, or variance of vector magnitude per octant.

6. The method of claim 1, wherein the spatio-temporal information of the VCG loops includes spatio-temporal distribution information of the VCG loops for both QRS VCG loops and T-wave VCG loops.

7. The method of claim 1, wherein the one or more trained machine learning models is trained using a gradient boosting method.

8. A system comprising:
    a set of electrodes configured to sense electrocardiogram (ECG) signals; and
    processing circuitry configured to:
        determine vectorcardiographic (VCG) signals as a function of the ECG signals, wherein the VCG signal comprise CCG loops;
        extract features from the VCG signals, wherein the extracted features comprise at least one of geometrical features of the VCG loops and/or spatio-temporal information of the VCG loops;
        detect, using one or more trained machine learning models, one or more myocardial infarctions (MI) based on the extracted features; and
        determine, using the one or more trained machine learning models, a MI location of the detected one or more myocardial infarctions based on the extracted features using the VCG signals and gradient boosting.

9. The system of claim 8, wherein the determination of the MI location includes identification of a region of a heart of where the one or more MI has occurred.

10. The system of claim 8, wherein the geometrical features include geometrical features of QRS VCG loops and T-wave VCG loops.

11. The system of claim 8, wherein the geometrical features include one or more of loop perimeter, loop centroid, maximum vector length, loop area, Ratio Perimeter/Area, Maximum distance between centroid and VCG loop, Angle between MVL and the different planes, Angle between QRS and T wave maximum vectors, or Angle between QRS and T wave optimal planes.

12. The system of claim 8, wherein the spatio-temporal information includes one or more of octant average vector length, maximum vector length (MVL) per octant, percentage of time per octant, or variance of vector magnitude per octant.

13. The system of claim 8, wherein the spatio-temporal information of the VCG loops includes spatio-temporal distribution information of the VCG loops for both QRS VCG loops and T-wave VCG loops.

14. The system of claim 8, wherein the one or more trained machine learning models is trained using a gradient boosting method.

15. A non-transitory computer-readable storage medium comprising instructions, that when executed, cause processing circuitry to:
   receive electrocardiogram (ECG) signals from a patient;
   determine vectorcardiographic (VCG) signals as a function of the ECG signals wherein the VCG signals comprise VCG loops;
   extract features from the VCG signals wherein the extracted features comprise at least one of geometrical features of the VCG loops and/or spatio-temporal information of the VCG loops;
   detect, using one or more trained machine learning models, one or more myocardial infarctions (MI) based on the extracted features; and
   determine, using the one or more trained machine learning models, an MI location of the detected one or more myocardial infarctions based on the extracted features.

16. The non-transitory computer-readable storage medium of claim 15, wherein the one or more trained machine learning models is trained using a gradient boosting method.

* * * * *